United States Patent [19]

Barham et al.

[11] 4,391,766

[45] Jul. 5, 1983

[54] EXTRACTION OF POLY(β-HYDROXYBUTYRIC ACID)

[75] Inventors: Peter J. Barham, Bristol; Alan Selwood, Harrogate, both of England

[73] Assignee: Imperial Chemical Industries PLC, London, England

[21] Appl. No.: 348,325

[22] Filed: Feb. 12, 1982

Related U.S. Application Data

[63] Continuation-in-part of Ser. No. 174,836, Aug. 4, 1980, Pat. No. 4,360,488.

[30] Foreign Application Priority Data

Aug. 13, 1979 [GB] United Kingdom ............... 7928172
Feb. 12, 1981 [GB] United Kingdom ............... 8104312

[51] Int. Cl.$^3$ ............................................. D01D 5/12
[52] U.S. Cl. ................................. 264/210.1; 264/211; 264/322; 528/189; 528/361; 528/491
[58] Field of Search ..................... 264/184, 210.1; 528/189, 361, 491

[56] References Cited

U.S. PATENT DOCUMENTS 4,140,741  2/1979  Lafferty et al. ............... 264/189
4,324,907  4/1982  Senior et al. .................. 528/361
4,358,583  11/1982  Walker et al. ................. 528/491

Primary Examiner—Jay H. Woo
Attorney, Agent, or Firm—Cushman, Darby & Cushman

[57] ABSTRACT

β-Hydroxybutyric acid polymers are extracted from micro-organism cells by contact with a solvent, such as 1,2-dichloroethane which is a poor solvent for the polymer once it has been precipitated.

The solution obtained by extraction is caused to gel and then solvent is expelled by subjecting the gel to a deformation process. Expelled solvent is recovered for extraction of polymer from a further quantity of cells.

10 Claims, No Drawings

EXTRACTION OF POLY(β-HYDROXYBUTYRIC ACID)

This application is a continuation-in-part of our co-pending Application Serial No. 174836 filed Aug. 4, 1980 now U.S. Pat. No. 4,360,488.

This invention relates to the extraction of poly(β-hydroxybutyric acid), and copolymers containing β-hydroxybutyric acid units and other hydroxycarboxylic acid units such as β-hydroxyvaleric acid units, from micro-organisms.

Poly(β-hydroxybutyric acid) is a thermoplastic polyester consisting of repeat units of the formula

which is accumulated by many micro-organisms, particularly bacteria, for example of the genera Alcaligenes, Athiorhodium, Azotobacter, Bacillus, Nocardia, Pseudomonas, Rhizobium, and Spirillium, as an energy reserve material.

The polymer is conveniently prepared by cultivating the micro-organism in an aqueous medium on a suitable substrate, such as a carbohydrate or methanol, as an energy and carbon source. The substrate must, of course, be one that is assimilable by the microorganism. In order to promote accumulation of the polymer, at least part of the cultivation is preferably conducted under conditions wherein there is a lamination of a nutrient that is essential for growth of the micro-organism but which is not required for polymer accumulation. Examples of suitable processes are described in European Patent Specification 15669 and in European Patent Application No. 81.303373, which is shortly to be published as specification No. 46344 and which corresponds to U.S. Application Ser. No. 291,762 filed Aug. 10, 1981.

Polymers containing both β-hydroxybutyric acid units and other hydroxycarboxylic acid units, such as β-hydroxyvaleric acid units, can also be produced microbiologically. Thus a microbiologically produced heteropolymer containing β-hydroxybutyric acid and β-hydroxyvaleric acid residues is described by Wallen et al in "Environmental Science and Technology" 8 (1974) 576-9. Also, as described in European Patent Application 81305186, corresponding to U.S. Application Ser. No. 319,673, various copolymers can be produced by cultivating the micro-organism on certain substrates, such as propionic acid which gives rise to β-hydroxyvaleric acid units in the copolymer.

Accordingly, in the present specification, by the term HB polymer we mean not only the homopolymer, poly(β-hydroxybutyric acid), but also copolymers as described above, provided that the β-hydroxybutyric acid residues form at least 50 mole %, and preferably at least 60, particularly at least 80, mole % of the polymer chain.

While cells containing the polymer can be used as such as a moulding material, for example as described in U.S. Pat. No. 3,107,172, it is generally desirable to separate the polymer from the remainder of the cell material.

Methods that have been proposed to effect this separation include breakage of the cells by methods such as treatment with acetone, followed by extraction of the polymer from the broken cells by treatment with a solvent in which the polymer is soluble. Examples of such processes are described in U.S. Pat. Nos. 3,036,959 and 3,044,942 in which the solvents employed are pyridine or mixture of methylene chloride and ethanol. Other extraction solvents for the polymer in the form in which it is produced in the cells include cyclic carbonates such as 1,2-propylene carbonate (see U.S. Pat. No. 4,101,533); chloroform (see U.S. Pat. No. 3,275,610); and 1,2-dichloroethane (see European Patent Specification 14490 and 15123).

U.S. Pat. No. 3,275,610 discloses other methods of cell breakage viz. ultrasonic vibration, grinding, French pressing, freezing/thawing cycles and lysozyme treatment, while, as described in the aforementioned European Patent Specification 15123, spray or flash drying of the suspension of cells as produced by culturing the micro-organism can also cause sufficient cell breakage to enable the polymer to be extracted from the cells.

In all these extraction processes a solution of the HB polymer in the solvent is formed: it is thus generally necessary to separate the HB polymer from the solution. This may be accomplished by adding the solution to a liquid in which the HB polymer is insoluble: thus when using chloroform or 1,2-dichloroethane, which we have found to be particularly suitable extraction solvents, the solution may be added to a methanol/water mixture. However such a precipitation method presents solvent recovery problems. Alternatively the HB polymer could be separated simply by evaporation of the solvent: however, as the extracted solutions are usually relatively dilute so that they can be readily filtered to remove any suspended microorganism cell fragments, such an evaporation process is not economic. Also, as the evaporation proceeds, the solution becomes increasingly viscous rendering the evaporation difficult. Generally the extracted solutions contain less than 10% by weight of HB polymer.

It would be desirable to devise a process in which the bulk of the solvent can be removed mechanically.

Solid HB polymers separated from micro-organism cells by solvent extraction followed by precipitation are crystalline, or partly crystalline, materials, melting at about 180° C. (β-hydroxybutyric acid homopolymer) or generally at somewhat lower temperatures in the case of copolymers. Freshly precipitated HB polymers are partially crystalline and crystalline further on heating to e.g. 100° C. or more. The difference in crystallinity is evident from the solubility characteristics of the polymer. For example freshly precipitated poly(β-hydroxybutyric acid) is soluble in chloroform at room temperature whereas the same material after heating for 30 minutes at 100° C. is not soluble in chloroform at room temperature. Methylene chloride will dissolve freshly precipitated poly(β-hydroxybutyric acid) at room temperature only if the polymer has not been allowed to become warmer than about 60° C. after precipitation. Freshly precipitated poly(β-hydroxybutyric acid) is not soluble at room temperature in 1,2-dichloroethane even if the precipitated polymer has not been allowed to warm to above 40° C. Chloroform, methylene chloride, and 1,2-dichloroethane do however dissolve poly(β-hydroxybutyric acid) at elevated temperatures, e.g. under reflux conditions. However poor solvents such as 1,2-dichloroethane can be used to extract poly(β-hydroxybutyric acid) from micro-organism cells even at relatively low temperatures, e.g. 10° to 40° C.: in the state in which the polymer exists in the microorganism cells, it is more readily dissolved by such solvents than after the polymer has been precipitated or otherwise separated from a solution thereof. This is presumably due to the configuration of the polymer in the micro-organism cells being different to that of polymer precipitated from a solution thereof.

In the parent Application Serial No. 174836 we disclose that a solution of poly(β-hydroxybutyric acid) in a poor solvent, such as 1,2-dichloroethane, in which freshly precipitated poly(β-hydroxybutyric acid) that has not been heated to above 40° C. is not soluble at temperatures below 25° C., can be caused to gel. By the term "not soluble" we mean that the solubility of the polymer in the solvent is less than 0.1% by weight. It is also disclosed in that Specification that such gels were free draining and, if subjected to a non-random deformation process, such as pressing, a substantial proportion of the solvent could be expelled therefrom. This expelled solvent is substantially free of dissolved polymer.

Such a process can thus be used in a process for the extraction of HB polymers to remove the bulk of the solvent from a solution of the HB polymer in an extraction solvent that is a poor solvent for the freshly precipitated HB polymer.

Accordingly the present invention provides a process for the separation of an HB polymer from micro-organism cells comprising
(a) extracting the HB polymer from the cells by contacting the HB polymer-containing cells with a solvent in with the HB polymer in the cells is soluble at the extraction temperature but in which the HB polymer which has been freshly precipitated and not heated to above 40° C. is not soluble at temperatures below 25° C.,
(b) separating the solution of the HB polymer in said solvent from the micro-organism cell residue,
(c) causing said solution to gel,
(d) subjecting said gel to a non-random deformation process whereby the bulk of the solvent is expelled from said gel, and
(e) using at least the bulk of said expelled solvent for extraction of the HB polymer from a further quantity of the HB polymer-containing cells.

For use as a thermoplastic coulding material, the HB polymer is desirably in granulated or powder form so that it can readily be fed to thermoplastic processing equipment. Granulation may be effected by feeding the deformed gel to an extruder, in which the deformed gel is preferably heated to above 150° C. The extrudate is then cut into granules by means that are well known in the art such as a die face cutter.

The deformed gel, which was referred to in aforesaid parent application No. 174836 as a "parchment" although it will be appreciated that it may have any suitable physical shape, generally contains some residual solvent. The amount of residual solvent in the deformed gel may be as much as 70% by weight of the deformed gel. The extruder used in the granulation step may be provided with a vent or other volatiles extraction means to permit removal of at least some of the residual solvent.

Additives, such as stabilisers, e.g. as a solution thereof in a suitable solvent, may be added to the deformed gel before, or during, its passage through the extruder. Where residual solvent is recovered from the deformed gel e.g. through the vent of a vented extruder, and is used for further extraction of the HB polymer from micro-organism cells, if additives are incorporated as a solution, the solvent of the additive solution should be that used for the extraction of the HB polymer from the micro-organism cells.

Where the HB polymer is to be blended with one or more other polymers, for example as described in European Patent Application No. 81305188 corresponding to U.S. Application Ser. No. 320,127, the blending may be accomplished by extruding said other polymer and mixing the deformed gel with said other polymer before or during passage of the latter through the extruder.

As described in European Patent Specification 15123 the extraction of the HB polymer from the micro-organism cells may be effected by contacting an aqueous suspension of the cells, where necessary after a cell disruption step, with 1,2-dichloroethane, or by contacting cells that have been dried, e.g. by spray drying, with the extraction solvent. In the latter case the dried cells are preferably contacted with a solvent, such as acetone or methanol, in which the HB polymer is insoluble, to extract lipids prior to contact with the extraction solvent.

In either process the amount of HB polymer-extraction solvent employed is preferably such that the HB polymer content of the resultant solution is between 0.5 and 10% by weight. With more dilute solutions it is difficult to make a satisfactory gel that can be handled in the deformation process without an intermediate, and uneconomic, evaporation step, while with more concentrated solutions the extraction effeciency may be impaired and furthermore the resulting solution may be too viscous to be readily filtered or otherwise separated from the bacterial cell residue.

After separation of the solution of the HB polymer in the extraction solvent from the micro-organism cell residue, the solution is caused to gel. Gelation may be brought about by subjecting the solution to conditions which cause crystallisation of the HB polymer.

By the term "gel" is meant a three-dimensional network of polymer chains in an environment of the "solvent" in which a significant number of the polymer chains contain at least three linking points along their length which are linked to other polymer chains. The polymer chains may be molecular in nature or may consist of fibrils made up of molecular chains. The gels used in the invention are so viscous that they are capable of supporting a stainless steel ball bearing 1.5 mm in diameter whilst the gel still contains solvent. The gels are also preferably coherent in that they can be picked up with forceps without the gel disintegrating to any substantial extent. While coherent gels which are able to support a stainless steel ball bearing of 1.5 mm diameter are readily obtained using concentrations of 1% or more by weight of the HB polymer at lower concentrations the gel will readily support the ball bearing but it may not be possible to remove a coherent gel from its surrounding solvent using forceps.

The solutions may be caused to gel by a number of methods which may be used singly or in combination. For example gelation may be induced by allowing the solution to stand at a temperature between 10° C. and 30° C., optionally with one or more of the following preliminary steps:
(i) cooling the solution to below 0° C.
(ii) shearing the solution, e.g. by stirring, and
(iii) seeding the solution with a preformed gal of the HB polymer.

The time taken to produce a gel depends on, inter alia, the gelation inducing conditions and the concentration of the solution. Thus while a solution may gel simply by storage at room temperature for several days, gelation may be induced in an identical solution by cooling and/or stirring for an hour or two.

In order to produce a gel spontaneously on storage at room temperature the HB polymer concentration of the solution must be at least 1.5% by weight. For solutions of lower concentration gelation only occurs if an additional step, such as shearing or cooling is applied.

The preferred methods of inducing gelation of the HB polymer are shearing and/or cooling, followed by standing at a temperature between 10° C. and 30° C.

During formation of the gel, some syneresis may occur. The separated solvent may be removed (for re-ise if desired) prior to subjecting the gel to the non-random deformation process.

The non-random deformation process used in the invention is a process in which, for example, the gel is subjected to bulk deformation, such as by pressing the gel between opposed surfaces (as in compression moulding, calendering and extrusion), or to a tensile deformation such as by drawing a fibre or film from the gel. It does not include random deformation processes such as the type of deformation experienced when a gel is sheared in a mixing process in which mixing vortices are created by the motion of a stirrer or in a process in which the gel is, in effect, cut by rows of pegs or a breaker plate.

In order to effect the non-random deformation process to expel solvent from the gel, the latter may be pressed in a simple press or passed between a pair of rotating rollers. Preferably the gel is deformed while in contact with at least one porous member: for example at least one of the opposed surfaces in a press or at least one of a pair of rollers is porous. Provided the pore size is not too large and/or the gel is not too weak (as is obtained with very dilute solutions), the gel maintains its integrity and substantially no polymer enters the pores. Suitably the pore size is below 25 $\mu$m.

The pressure applied during the squeezing operation should be sufficient to expel sufficient of the solvent to give a deformed gel containing less than 70% by weight residual solvent. Generally the applied pressure need not exceed 50 kg cm$^{-2}$ and is preferably in the range of 5 to 50 kg cm$^{-2}$. The deformation operation is preferably conducted at temperatures in the range 10° to 30° C.

During the deformation process the bulk of the solvent present in the original solution is expelled and the expelled solvent contains virtually no HB polymer. Thus if a solution containing 5% by weight of HB polymer is caused to gel and the gel is subjected to a non-random deformation process to give a product (i.e. the deformed gel) containing 50% by weight of the HB polymer the amount of solvent separated (by expulsion during the deformation process and, where it occurs, by syneresis during gel formation) is thus about 95% by weight of the solvent present in the original solution.

The deformed gel can be further processed, e.g. granulated as hereinbefore described, or formed into shaped articles e.g. by orienting uniaxially or biaxially, e.g. by cold rolling or drawing, preferably at temperatures below 160° C. to give tough films, fibres or other shaped articles. Advantage may be taken of residual solvent in the deformed gel by conducting the shaping operations at low temperatures, including room temperature, and allowing the residual solvent to evaporate after shaping.

During such further processing residual solvent may be removed, e.g. by the use of vented extruders as mentioned hereinbefore, or by simple drying.

At least the bulk, i.e. over 50% by weight, of the solvent expelled during the deformation step, if desired together with some or all of the solvent separated, if any, by syneresis on formation of the gel and/or some or all of any solvent recovered from the further processing of the deformed gel, is used for the extraction of the HB polymer from a further quantity of the microorganism cells, together with such quantity of fresh solvent as may be necessary. Where the process is operated continuously the solvent is thus recycled. While all of the recovered solvent may be re-used, preferably a portion thereof is bled off to avoid undue build-up of contaminants. After removal of any such contaminants some or all of this purified solvent can be re-used for extraction. Hence we prefer that at least part of the re-used solvent is subject to purification, e.g. by distillation, prior to being re-used for extraction. If necessary all the solvent to be re-used may be subjected to purification before re-use.

The invention is illustrated by the following example.

An aqueous suspension of *Alcaligenes eutrophus* of 150 gl$^{-1}$ biomass content, of which about 45% by weight was poly($\beta$-hydroxybutyric acid), was spray dried at a suspension feed rate of 5000 ml h$^{-1}$, an air inlet temperature of 240° C., an air outlet temperature of 110° C., and an air flow rate of 300 m$^3$ h$^{-1}$. The resultant powder consisting of the dried cells had a particle size below 150 $\mu$m.

20 g of the dried cells were refluxed with 400 ml of methanol for 5 minutes to extract lipids and then the residual cells filtered from the methanol. The residual cells were then divided into two equal portions.

One portion was refluxed with 200 ml of 1,2-dichloroethane for 15 minutes and then the 1,2-dichloroethane solution was separated from the cell debris by filtration. The resulting solution contained about 1.8% by weight of poly($\beta$-hydroxybutyric acid).

The solution was then rapidly cooled to below 0° C. using a solid carbon dioxide/methanol freezing mixture. After 5 minutes immersion in the freezing mixture the solution froze solid. The frozen solution was then warmed to 20° C. over a period of 20-30 minutes whereupon it was found that a coherent gel had formed, with some syneresis; the separated solvent, about 40 ml, was poured off.

The residual gel was pressed for 60 seconds in a press at 20° C. at a pressure of about 10$^6$ Nm$^{-2}$ gauge. During pressing a considerable amount of solvent was expelled. About 140 ml of expelled solvent was collected. The expelled solvent, and that separated by syneresis, both contained less than 0.1% by weight of poly($\beta$-hydroxybutyric acid).

On opening the press, a parchment-like sheet of the pressed gel weighing about 11 g was obtained. This sheet contained about 64% by weight of 1,2-dichloroethane.

The residual solvent was removed from the parchment by volatilisation during drying the parchment in an oven at 100° C., to give a sheet of poly($\beta$-hydroxybutyric acid) weighing about 4 g. No attempt was made to recover the volatilised solvent.

The total amount of solvent recovered was thus about 180 ml, i.e. 90% of that originally employed. Apart from the solvent lost during the drying step (about 5.6 ml), the remainder was lost during the filtration step and by failure to collect all the solvent expelled during the pressing step.

By addition of 20 ml of fresh 1,2-dichloroethane to the recovered solvent, the resultant 200 ml of solvent could be used to repeat the above extraction, gelation and pressing procedure to extract the poly($\beta$-hydroxybutyric acid) from the other portion of the lipid-extracted dried cells.

We claim:

1. A process for the separation of a polymer containing at least 50 mole % of $\beta$-hydroxybutyric acid residues in the polymer chain from micro-organism cells comprising
   (a) extracting the polymer from the cells by contacting the polymer-containing cells with a solvent in which the polymer is soluble at the extraction temperature but in which extracted polymer, which has been freshly precipitated and not heated to above 40° C., is not soluble at temperatures below 25° C.,
   (b) separating the solution of the polymer in said solvent from the micro-organism cell residue,
   (c) causing said solution to gel,
   (d) subjecting said gel to a non-random deformation process whereby the bulk of the solvent is expelled from said gel, and
   (e) using at least the bulk of said expelled solvent for extraction of polymer from a further quantity of the polymer-containing cells.

2. A process according to claim 1 wherein the amount of solvent used to extract the polymer is such that the resultant solution contains 0.5 to 10% by weight of the polymer.

3. A process according to claim 2 wherein the amount of solvent used to extract the polymer is such that the resultant solution contains at least 1.5% by weight of the polymer.

4. A process according to any one of claims 1 to 3 wherein gelation is effected by allowing the solution to stand at a temperature between 10° C. and 30° C., optionally with one or more of the following preliminary steps:
   (i) cooling to below 0° C.
   (ii) shearing, and
   (iii) seeding with a preformed gel of the polymer.

5. A process according to claim 1 wherein the gel is deformed while in contact with at least one porous member.

6. A process according to claim 1 wherein the deformed gel is extruded.

7. A process according to claim 6 wherein at least some of the solvent in the deformed gel is volatilised and removed during the extrusion step.

8. A process according to claim 6 or claim 7 wherein a solution of an additive in the solvent is added to the deformed gel before, or during, the extrusion step.

9. A process according to claim 1 wherein the solvent used for the extraction of the polymer from a further quantity of the polymer-containing cells comprises (a) the bulk of the solvent expelled during the deformation step together with (b) at least one of
   (i) solvent expelled by syneresis during gel formation,
   (ii) solvent recovered during further processing of the deformed gel, or
   (iii) fresh solvent.

10. A process according to claim 1 wherein the solvent used for the extraction of the polymer from a further quantity of the polymer containing cells comprises
    (a) recovered solvent alone or together with
    (b) fresh solvent, said recovered solvent consisting of
        (i) the bulk of the solvent expelled during the deformation step, alone or together with at least one of
        (ii) solvent expelled by syneresis during gel formation and
        (iii) solvent separated during further processing of the deformed gel, and at least part of said recovered solvent is purified prior to its use for said extraction or polymer from the further quantity of polymer-containing cells.

* * * * *